United States Patent
Rattner

[11] Patent Number: 5,699,804
[45] Date of Patent: Dec. 23, 1997

[54] THERAPY APPARATUS HAVING A SOURCE OF ACOUSTIC WAVES

[75] Inventor: Manfred Rattner, Grossenseebach, Germany

[73] Assignee: Siemens Aktiengesellschaft, Munich, Germany

[21] Appl. No.: 645,504

[22] Filed: May 14, 1996

[30] Foreign Application Priority Data

Jun. 7, 1995 [DE] Germany ............ 195 20 749.1

[51] Int. Cl.$^6$ ................................. A61B 8/00
[52] U.S. Cl. ............... 128/660.03; 128/653.1; 128/662.03; 601/3; 601/4
[58] Field of Search ............ 128/660.03, 661.01, 128/661.03, 662.03, 660.07, 653.1; 601/2–4; 607/97

[56] References Cited

U.S. PATENT DOCUMENTS

| | | |
|---|---|---|
| 4,697,588 | 10/1987 | Reichenberger . |
| 4,928,672 | 5/1990 | Grasser et al. . |
| 5,060,650 | 10/1991 | Wurster et al. ............ 128/660.03 |
| 5,065,762 | 11/1991 | Ifflaender et al. .......... 128/660.03 |
| 5,243,985 | 9/1993 | Aida et al. ............... 128/660.03 |
| 5,329,930 | 7/1994 | Thomas, III et al. ........ 128/661.01 |
| 5,391,140 | 2/1995 | Schaetzle et al. ............... 601/4 |
| 5,419,327 | 5/1995 | Rohwedder et al. ......... 128/660.03 |

*Primary Examiner*—Ruth S. Smith
*Attorney, Agent, or Firm*—Hill, Steadman & Simpson

[57] ABSTRACT

A therapy apparatus has a source of acoustic waves with an X-ray-transparent region. An X-ray-transparent diagnostic ultrasound transducer of an ultrasound locating system is contained in this region. The X-ray-transparent diagnostic ultrasound transducer can be a piezoelectrically activated polymer foil.

6 Claims, 2 Drawing Sheets

5,699,804

THERAPY APPARATUS HAVING A SOURCE OF ACOUSTIC WAVES

BACKGROUND OF THE INVENTION

1. Field of the Invention

The present invention is directed to therapy apparatus of the type having a source of acoustic waves with a region transparent to X-rays and having a diagnostic ultrasound transducer belonging to an ultrasound locating means.

2. Description of the Prior Art

A therapy apparatus of the above type, provided for operation with an X-ray locating means, is described, e.g., in European Application 0 400 196. An advantage of a therapy apparatus of this type is that a compact construction is possible. Moreover, obstacles in the propagation path of the acoustic waves, as the beam of the X-ray locating means travels through the X-ray-transparent region of the source, are particularly easy to recognize in the image of the X-ray locating means. In addition, it is possible to introduce the diagnostic ultrasound transducer of the ultrasound locating means into the X-ray-transparent region, so that it is also possible to locate a region to be treated by means of ultrasound. Simultaneous ultrasound and X-ray locating is not possible, however, with the X-ray locating beam travelling through the X-ray transparent region of the source.

In order to remedy this, it is known, e.g., from German OS 39 16 093, to arrange the diagnostic ultrasound transducer of the ultrasound locating means fixedly in the source, outside the X-ray-transparent region. A simultaneous operation of the X-ray and ultrasound locating means is indeed possible in this way, but the "lines of sight" of the X-ray and ultrasound locating means deviate more or less strongly from one another. In addition, the diagnostic ultrasound transducer is located inside the region traversed by the acoustic waves, so that it disturbs their propagation. In some circumstances it is even necessary to take measures to protect the diagnostic ultrasound transducer from being damaged by the acoustic waves from the source.

SUMMARY OF THE INVENTION

An object of the present invention is to provide a therapy apparatus of the type described above wherein simultaneous operation of the X-ray and ultrasound locating means is possible, but the diagnostic ultrasound transducer of the ultrasound locating means is not located in the propagation path of the acoustic waves from the source.

This object is achieved according to the invention in a therapy apparatus having a source of acoustic waves with a region transparent to X-rays, in which an X-ray-transparent diagnostic ultrasound transducer of an ultrasound locating means is contained. As a result of the use of an X-ray-transparent diagnostic ultrasound transducer, this transducer can thus be arranged in the X-ray-transparent region of the source in the inventive therapy apparatus, and can remain in that region even during the operation of the X-ray locating means. Simultaneous operation of the X-ray and ultrasound locating means is thus possible without the diagnostic ultrasound transducer of the ultrasound locating means being located in the region traversed by the acoustic waves. Moreover, the X-ray and ultrasound locating ensue with essentially the same "line of sight."

In a preferred embodiment of the invention, a piezoelectrically activated polymer foil, made e.g. of polyvinylidene-fluoride (PVDF), is provided as an X-ray-transparent diagnostic ultrasound transducer. Polymer foils of this type are known e.g. from German OS 42 41 161, in which they are used as pressure sensors that serve for the reception of reflected shock waves. They do not significantly weaken the X-ray radiation of the X-ray locating means, and thus have no disadvantageous effect on the image quality of the X-ray locating means. The electrical contacting required for the connection of the polymer foil with the electronics of the ultrasound locating means also presents no problem with regard to the image quality of the X-ray locating means, in particular if, according to a version of the invention, the polymer foil is provided with foil-type metal electrodes for the electrical contacting.

According to further embodiments of the invention, the ultrasound locating means operates in the A mode and/or in the B scan mode. In the first case, there ensues only a transit-time measurement of the diagnostic ultrasound waves reflected at the respective region to be treated, which permits determination of the distance of the region to be treated from the source of acoustic waves. In the second case, sectional images of a body region traversed by the ultrasound waves are generated, which give corresponding pictorial information concerning the position of the region to be treated, insofar as this region is located in the body region traversed by the diagnostic ultrasound waves.

If a piezoelectrically activated polymer foil is provided as an X-ray-transparent diagnostic ultrasound transducer, according to an embodiment of the invention the foil-type metal electrodes are arranged such that the piezoelectrically activated polymer foil is divided into a plurality of transducer elements that can be driven in the manner of a phased array (driving the transducer elements with respective phase shifts). It is then possible to scan the respective object to be treated by means of the diagnostic ultrasound waves in the way required for the generation of a desired ultrasound sectional image, without having to reposition the diagnostic ultrasound transducer mechanically. In addition, it is possible to electronically focus the diagnostic ultrasound waves. The phased array can be an annular array or a linear array.

DESCRIPTION OF THE PREFERRED EMBODIMENTS

Figure 1:
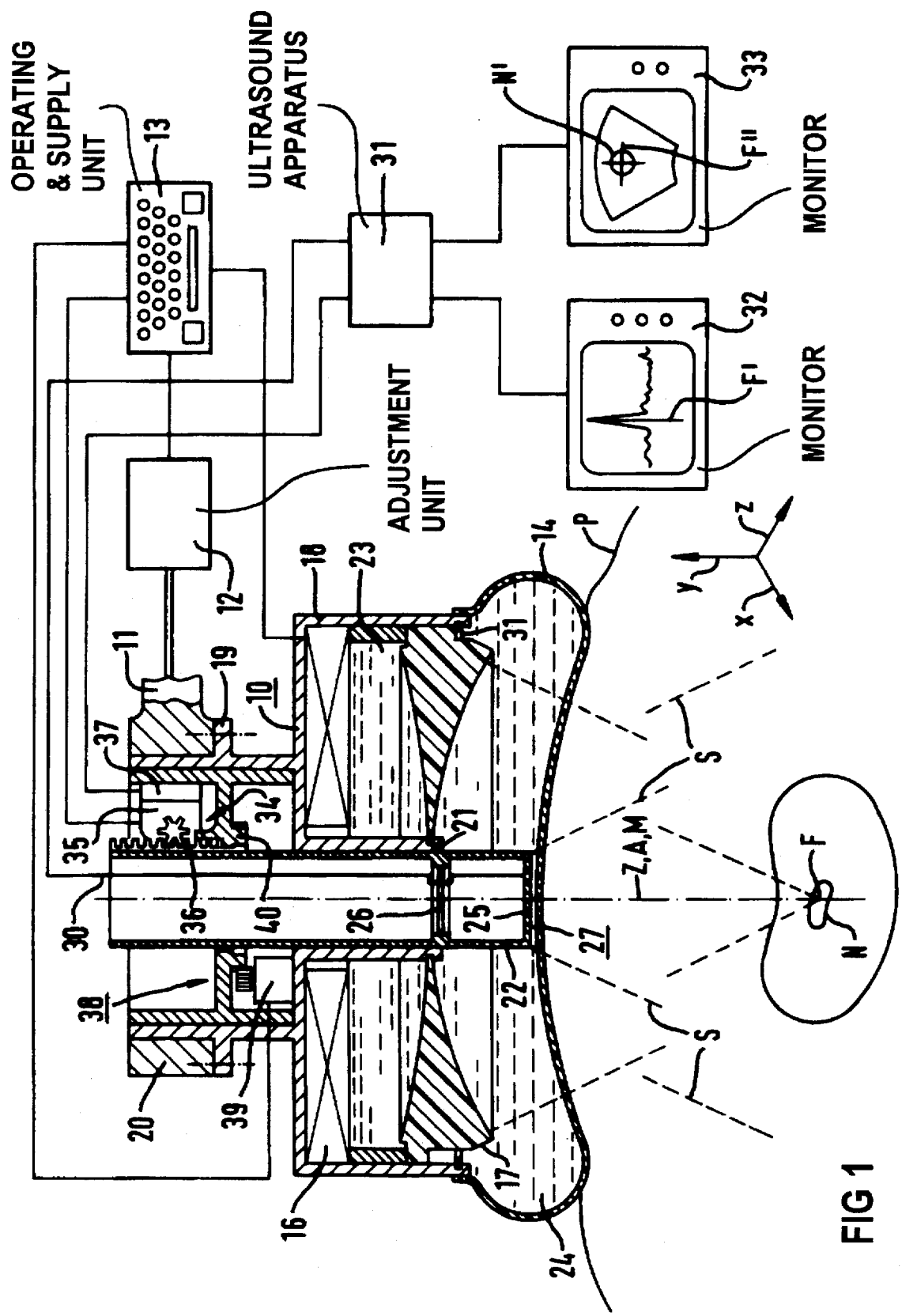
FIG. 1 shows an inventive therapy apparatus partly in section, and partly schematically.

As shown in FIG. 1, the inventive therapy apparatus includes a source of focused acoustic waves, designated as a whole by 10, which is attached via a mount 11 to an adjustment unit 12, shown only schematically. This permits the movement of the source 10 in the direction of the x, y and z axes of the spatial coordinate system indicated in FIG. 1. An operating and supply unit 13 is connected to the adjustment unit 12, which contains all the power connections, driver circuits, control circuits, etc. necessary for the operation of the source 10, and which is provided with a keyboard for the operation of the therapy apparatus. The source 10 contains a central X-ray-transparent region, described in more detail below, and is aligned in relation to an X-ray locating means (not shown) such that the central beam Z thereof, indicated by a broken line in FIG. 1, runs through the X-ray-transparent region. The source 10 lies on the body surface of a patient P with an X-ray-transparent coupling cushion 14, in order enable the focused acoustic waves generated in the operation of the therapy apparatus to be introduced into the body of the patient P, to treat e.g. a renal calculus.

As can be seen in FIG. 1, the source 10 of focused acoustic waves contains a pressure pulse source 16 (not shown in more detail) and an acoustic converging lens 17. The converging lens 17 focuses the pressure pulses emanating from the pressure pulse source 16 on a focus F; in practice this is a spatial (three-dimensional) focus zone. The focus F lies on the acoustic axis A of the source 10, corresponding to the center axis M of the source 10. The source 10 is constructed approximately rotationally symmetrically with respect to the center axis M. The pressure pulse source 16 and the converging lens 17 are contained in a housing 18, which is closed fluid-tight at its end farthest from the pressure source 16 by means of the elastic, flexible coupling cushion 14. The pressure pulse source 16 is, for example, an electromagnetic pressure pulse source, as described with respect to structure and function in European Applications 0 188 750 and in 0 301 360. The high-voltage pulse generator, required for the operation of the pressure pulse source 16, is a component of the operating and supply unit 13, with which the pressure pulse source 16 is connected via a corresponding circuit.

At its other end, adjacent to the pressure pulse source 16, the housing 18 has a mounting flange 19, which serves for fastening the source 10 to a mounting ring 20 of the carrier 11 by means of screws (in FIG. 1 only the center lines of two screws are indicated by broken lines).

The space between the pressure pulse source 16 and the converging lens 17, as well as that between the converging lens 17 and the coupling cushion 14, are filled with an acoustic propagation medium. In the case of the specified exemplary embodiment, both spaces contain the same acoustic propagation medium, namely water 23 and 24. The two spaces filled with water 23 and 24 are divided from one another by the converging lens 17 in the case of the specified exemplary embodiment. They can alternatively be connected with one another, in particular if both spaces contain the same acoustic propagation medium.

The converging lens 17 is a biconcavely shaped lens made of solid material, e.g., polystyrene, having speed of sound propagation therein which is larger than that of the water 23 and 24 provided as an acoustic propagation medium.

A cup-shaped tube 22, made of an X-ray-transparent material such as Plexiglas®, is formed in a cylindrically tubular inner wall 21 of the housing 18. The tube 22 is rotatable in the bore of the inner wall 21, and can be axially displaced and is contained in a fluid-tight fashion, possibly with the use of sealing means (not shown).

The region of the source 10 located inside the inner wall 21 is the aforementioned X-ray-transparent region, which is maintained free of propagation medium by means of the tube 22 in order to avoid negative influences on the image quality. For this purpose, when the source 10 is applied to the body surface of the patient P indicated in FIG. 1, the tube 22 is pushed into the bore of the inner wall 21 to such an extent that its base 25 touches the body surface of the patient P, with the interposition of the coupling cushion 14.

The therapy apparatus and the X-ray locating means are aligned relative to one another such that the central beam Z of the X-ray examination apparatus coincides with the acoustic axis A of the therapy apparatus, whereby the latter is at the same time the center axis M of the X-ray-transparent region.

In the tube 22, an X-ray-opaque mark is disposed at some distance from the base 25 of the tube, this mark lying on the acoustic axis A and thereby on the central beam Z of the X-ray locating means. In the case of the specified exemplary embodiment, this is a lead cross 26 formed from two lead wires, which intersect at a point lying on the acoustic axis A.

On the outside of the base 25 of the tube 22, an X-ray-transparent diagnostic ultrasound transducer is attached, designated as a whole with 27.

Figure 2:
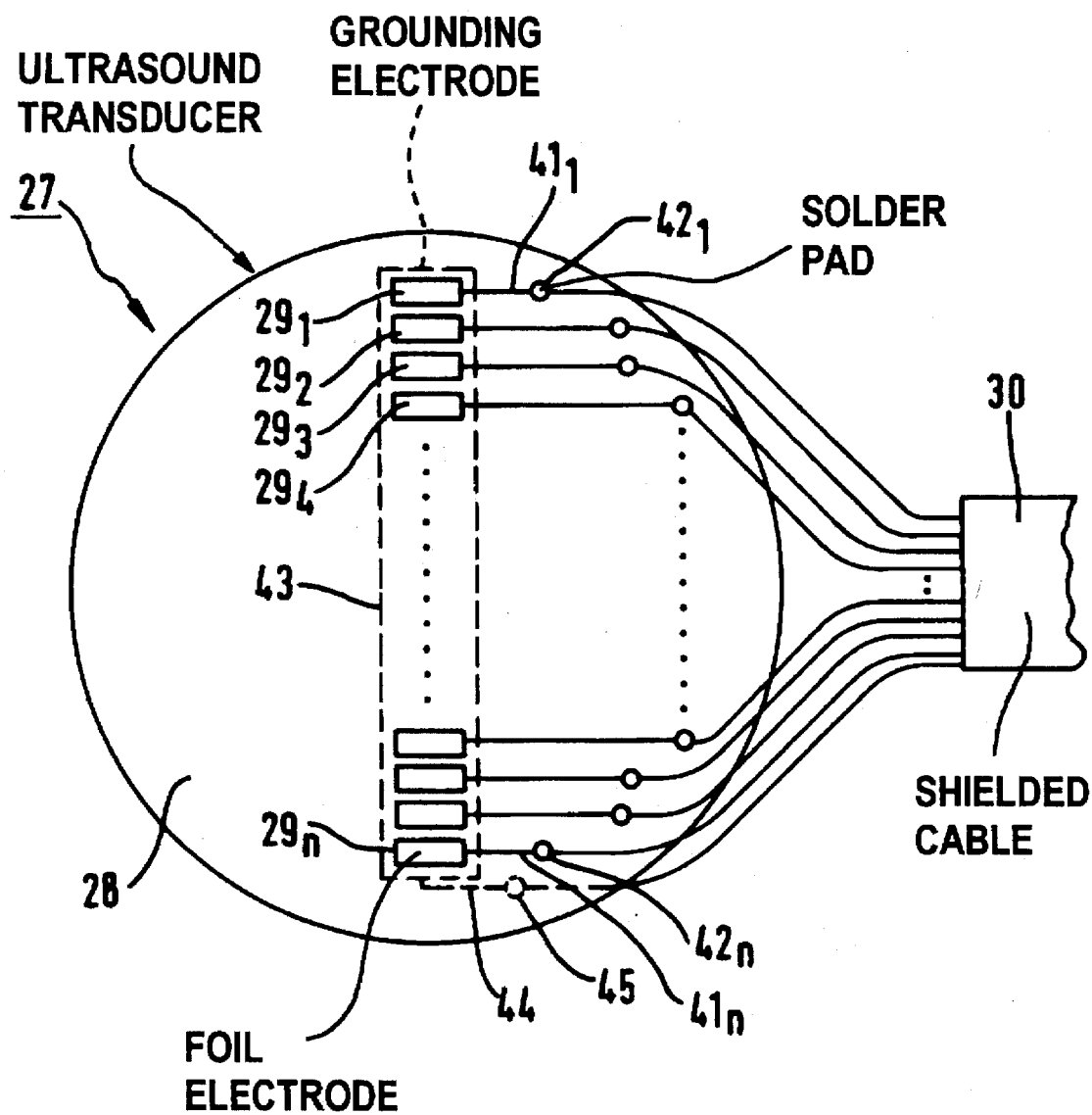
FIG. 2 shows the diagnostic ultrasound transducer of the therapy apparatus according to FIG. 1, in a schematic representation.

According to FIG. 2, the X-ray-transparent diagnostic ultrasound transducer 27 is a piezoelectrically activated PVDF foil 28, provided with a number of foil-type metal electrodes $29_1$ to $29_n$ and thus divided into transducer elements, as is likewise illustrated in FIG. 2, these elements forming a linear array in the case of the specified exemplary embodiment. The metal electrodes $29_1$ to $29_n$ are connected via corresponding printed conductors $41_1$ to $41_n$ and soldering pads $42_1$ to $42_n$ to a multiwire shielded cable 30. The shielded cable 30, as shown in FIG. 1, is laid along the inner wall of the tube 22 and connects the diagnostic ultrasound transducer 27 with an ultrasound apparatus 31, constructed in a known manner. In addition, on the back side of the PVDF foil a large-surface metallic grounding electrode 43 is arranged, indicated in FIG. 2 by broken lines, which overlaps with the metal electrodes $29_1$ to $29_n$. The grounding electrode 43 is connected via a printed conductor 44 and a soldering pad 45 (both likewise indicated in FIG. 2 with broken lines) with the cable 30 and thus with the ultrasound apparatus 31.

The ultrasound apparatus 31 and the ultrasound transducer 27 can operate together, in the A mode or in the B scan mode.

In the A mode, the ultrasound apparatus 31 drives the ultrasound transducer 27 such that the transducer emits an ultrasound pulse. Subsequently, the portions of the ultrasound pulse reflected in the body of the patient, insofar as they reach the diagnostic ultrasound transducer 27, are converted by the transducer 27 into corresponding electric signals that proceed to the ultrasound apparatus 31, which displays the amplitude curve of these signals on a monitor 32.

In the image on the monitor 32, the ultrasound apparatus 31 mixes in a linear mark F', which marks that point of the represented amplitude curve that corresponds to the position of the focus F of the focused acoustic waves.

This process of emission of an ultrasound pulse and reception of the corresponding reflections is periodically repeated such that a continuous image results on the monitor 32.

In the A mode, it is indeed possible in principle to drive the transducer elements of the PVDF foil 28 simultaneously for generating the ultrasound pulse, e.g. in parallel, however, in the case of the specified exemplary embodiment the individual transducer elements of the PVDF foil 28 are driven by the ultrasound apparatus 31 in a phase-shifted manner, as a phased array, so that the generated ultrasound pulse is focused on the focus F of the source 10. Preferably, operation also takes place with the same phase-shift in the reception of the reflected portions of the generated ultrasound pulse. Thus it is achieved that the sensitivity in the relevant region surrounding the focus of the source 10 is at its highest during locating.

The transducer elements of the PVDF foil 28 are likewise driven in the manner of a phased array when the ultrasound locating means is operating in the B scan mode. The phase-shifted driving then ensues in a known manner, such that the generated diagnostic ultrasound scans a body layer of the patient P containing the focus F of the focused acoustic waves, and such that the ultrasound device 31 generates a sectional image of the scanned body layer on the basis of the output signals of the ultrasound transducer 27 corresponding to the reflections received by the ultrasound transducer 27. The sectional image is displayed on a monitor 33, in which the ultrasound apparatus 31 mixes a mark F''' that corresponds to the position of the focus F of the focused acoustic waves in the scanned body layer.

In the specified exemplary embodiment, the body layer scanned in the B scan mode contains not only the focus F but also the acoustic axis A. In the specified exemplary embodiment, the scanning of the body layer ensues in the form of a sector scan; the lateral boundary lines of the scanned circular sector are depicted in FIG. 1 in broken lines and designated with S. It is also possible, however, to drive the transducer elements of the PVDF foil 28 in the manner of a parallel scan.

If, in the B scan mode, groups of transducer elements are driven in the manner of a phased array rather than driving the transducer elements individually, the ultrasound from each group can be focused on the focus F of the source 10, in a way similar to that described above in connection with the A mode, in order to obtain an improved resolution of the ultrasound images in this region.

In order to ensure that the ultrasound transducer 27 lies snugly on the body surface of the patient P with the interposition of the coupling cushion 14 in the way required for obtaining good quality ultrasound images, a further adjusting mechanism 34 is provided, by means of which the tube 22 can be moved in the axial direction. The adjusting mechanism 34 contains an electromotor 35 provided with a pinion, which operates in combination with a rack 36 provided on the tube 22. A position transmitter 37 is allocated to the adjusting mechanism 34, the transmitter 37 emitting a signal corresponding to the axial position of the tube 22 to the ultrasound apparatus 31, which mixes the marks F' and F''' into the images of the monitors 32 and 33, taking into account the momentary position of the tube 22 and thus of the ultrasound transducer 27. In the focusing of the ultrasound pulses generated by means of the diagnostic ultrasound transducer, the signal of the position transmitter 40 is also taken into account.

In order to enable scanning of different layers containing the acoustic axis A using the ultrasound transducer 27, the tube 22 can be rotated around the acoustic axis A by means of an adjusting mechanism 38. The adjusting mechanism 38 contains an electromotor 39 provided with a pinion, which operates in combination with a component provided with a gear ring 40. This component is rotationally contained in the housing 18 and is connected in a torsionally strong manner with the tube 22 via a rack 36 that engages in a groove of the component.

The electromotors 35 and 39 of the adjusting mechanisms 34 and 38 are connected with the operating and supply unit 13 via corresponding circuits.

For the treatment of a patient P, the patient is first suitably positioned on a treatment table (not shown), in such a way that the kidney containing the renal calculus N is located approximately in the region of the central beam Z of the X-ray locating means, or, of the acoustic axis A of the source 10. The X-ray locating means is then activated. The source 10 is now moved across the direction of the acoustic axis A and of the central beam Z in the x and/or z direction relative to the patient P, such that in the X-ray image generated by the X-ray locating means the image of the lead cross 26 coincides with the image of the renal calculus N, signifying that the renal calculus N lies on the acoustic axis A. The X-ray locating means is preferably an X-ray diagnostic means having an X-ray image intensifier with a subsequent video apparatus, so that the generated X-ray images can be displayed on a corresponding monitor. In order to avoid exposing the patient P unnecessarily to X-ray radiation, the X-ray locating means is deactivated after this image is obtained.

The source 10 is then moved backwards in the direction of the acoustic axis A and the central beam Z, i.e. in the direction of the y axis, until the source 10, with its coupling cushion 14, lies snugly on the body surface of the patient P. The tube 22 is moved in the direction of the patient P far enough so that the tube 22 lies snugly on the body surface of the patient P, with the interposition of the coupling cushion 14.

When this is the case, the X-ray locating means is again activated, and on the basis of the corresponding X-ray image it is again checked whether the image of the lead cross 26 still coincides with the image of the renal calculus N. If displacements have occurred as a result of the described coupling process, these are corrected by moving the source 10 in the direction of the x and z axes. The X-ray locating means is then again deactivated.

The ultrasound locating means is then activated. By means of the ultrasound locating means, the source 10 can now easily be positioned so that the region to be treated, i.e. the renal calculus N in the case of the specified exemplary embodiment, is located in the focus F of the pressure pulses.

If the ultrasound locating means is operating in the B scan mode, this takes place by moving the source 10 in the y direction in such a manner that the image N' of the renal calculus N coincides with the marking F''' in the ultrasound image, in the way shown in FIG. 1.

If the ultrasound locating means is operating in the A mode, the source 10 is moved in the y direction in such a way that the amplitude maximum, achieved at the renal calculus N by means of the reflections of the ultrasound pulses emitted by the ultrasound transducer 27, coincides with the marking F', in the way shown in FIG. 1.

Of course, it is not necessary to use the two operational modes of the ultrasound locating means alternatively. Rather, a simultaneous use of both operational modes is also possible in the interest of a more precise locating, e.g. by alternating generating an ultrasound image in the A mode and an image in the B scan mode.

The lead cross 26 is not required if a mark identifying the position of the central beam Z or of the acoustic axis A is electronically mixed into the X-ray image in a known manner, or if the display screen of the X-ray locating means is provided with a suitable marking at the corresponding point, e.g. by means of an adhesive.

In the specified exemplary embodiment, the source is moved relative to the patient P, however, the source 10 can instead remain stationary and the patient P can be moved relative to the source, if the patient is positioned on a patient positioning means that is suitably adjustable. It is also possible to achieve the required adjustment of the source 10 and the patient P relative to one another by moving both the source 10 and the patient P.

In the specified exemplary embodiment, the converging lens 17 has a fixed focal length, however, it is also possible to use a variable-focus lens, i.e. a lens with an adjustable focal length. In this case, it must be ensured through suitable measures that the mixing in of the marks F' and F''' ensues in a manner that takes into account the currently set focal length of the variable-focus lens.

In the specified exemplary embodiment, it is possible to operate the ultrasound locating means both in the A mode and in the B scan mode, however, it is also within the scope of the invention to provide only one of these two modes, or to provide for alternative or additional ultrasound locating methods. For example, it is possible to generate the diagnostic ultrasound impulses, by operating the source 10 at reduced power instead of by means of the transducer 27, and to receive the corresponding reflections by the diagnostic ultrasound transducer 27.

In the specified exemplary embodiment, the source 10 contains an electromagnetic pressure pulse source. The inventive therapy apparatus can, however, contain a different type of pressure pulse source, e.g. a piezoelectrically operating pressure pulse source. It is also possible to provide, in place of a pressure pulse source, other sources of acoustic waves, e.g. an ultrasound source, which generates ultrasound in the form of continuous sound, ultrasound bursts or ultrasound pulses. It is possible in this case in particular to use the therapy apparatus for hyperthermia treatment processes. At the same time, it is clear that inventively constructed therapy apparatus can be used not only for lithotripsy, as specified in connection with the exemplary embodiment, but also for other medical purposes.

The thickness of the metal foils forming the metal electrodes $29_1$ to $29_n$, the grounding electrodes 43, the printed conductors $41_1$ to $41_n$ and 44, and the soldering pads $42_1$ to $42_n$ and 45 is dimensioned so that in no case do the foils disturb the image of the X-ray locating means significantly. The soldering pads are arranged in the edge area of the PVDF foil 28, in order to minimize disturbances of the image of the X-ray locating means by the leads of the cable 30.

Although modifications and changes may be suggested by those skilled in the art, it is the intention of the inventors to embody within the patent warranted hereon all changes and modifications as reasonably and properly come within the scope of their contribution to the art.

I claim as my invention:

1. A therapy apparatus for use with an X-ray locating system comprising:

a source of acoustic waves for treating a pathology located in a region of a patient, said source of acoustic waves having an X-ray transparent region formed by an opening extending through said source allowing unattenuated passage of X-rays through said opening; and ultrasound locating means for producing an ultrasound image of said region of said patient containing said pathology, said ultrasound locating means having a totally X-ray transparent diagnostic ultrasound transducer disposed in said opening.

2. A therapy apparatus as claimed in claim 1 wherein said X-ray transparent diagnostic ultrasound transducer comprises a piezoelectrically activated polymer foil.

3. A therapy apparatus as claimed in claim 2 wherein said piezoelectrically activated polymer foil comprises a plurality of foil-type metal electrodes, each forming an ultrasound transducer element.

4. A therapy apparatus as claimed in claim 1 wherein said ultrasound locating means comprises an A mode ultrasound locating means.

5. A therapy apparatus as claimed in claim 1 wherein said ultrasound locating means comprises an B mode ultrasound locating means.

6. A therapy apparatus as claimed in claim 1 wherein said X-ray transparent diagnostic ultrasound transducer comprises a plurality of foil-type metal electrodes respectively forming a plurality of transducer elements, and wherein said ultrasound locating means comprises means for driving said transducer elements as a phased array.

* * * * *